United States Patent [19]
Myers et al.

[11] Patent Number: 4,818,230
[45] Date of Patent: Apr. 4, 1989

[54] METHOD FOR REMOVING DECAY FROM TEETH

[76] Inventors: William D. Myers, 5855 Wingcroft Ct., Birmingham, Mich. 48010; Terry Myers, 1935 N. Pontiac Trail, Walled Lake, Mich. 48088

[21] Appl. No.: 85,235

[22] Filed: Aug. 12, 1987

Related U.S. Application Data

[63] Continuation-in-part of Ser. No. 808,542, Dec. 13, 1985, abandoned.

[51] Int. Cl.⁴ .............................................. A61C 5/00
[52] U.S. Cl. .................................. 433/215; 128/303.1
[58] Field of Search ..................... 433/215; 128/303.1, 128/365, 395

[56] References Cited

U.S. PATENT DOCUMENTS

| 4,273,535 | 6/1981 | Yamamoto et al. | 433/215 |
| 4,503,853 | 3/1985 | Ota et al. | 433/215 |
| 4,521,194 | 6/1985 | Myers et al. | 433/215 |

*Primary Examiner*—John J. Wilson
*Attorney, Agent, or Firm*—Gifford, Groh, Sheridan, Sprinkle and Dolgorukov

[57] ABSTRACT

The present invention provides a method for removing dental decay and carious lesions from human teeth. The method of the present comprises the steps of aiming a pulsed laser so that its output impinges upon the decay and thereafter repeatedly activating the laser in pulse mode until the decay is eradicated from the tooth.

8 Claims, 1 Drawing Sheet

METHOD FOR REMOVING DECAY FROM TEETH

CROSS REFERENCE TO RELATED APPLICATION

This application is a continuation-in-part of patent application Ser. No. 808,542, filed Dec. 13, 1985 and entitled Method for Removing Decay From Teeth, now abandoned.

BACKGROUND OF THE INVENTION

I. Field of the Invention

The present invention provides a method for removing decay and/or carious lesions from teeth and especially from human teeth.

II. Description of the Prior Art

Carious lesions or tooth decay is initiated by bacteria which reside in tooth plaque. These bacteria produce acids which diffuse through a matrix of water-protein-lipid and attack the hydroxyapatite crystals which form the tooth enamel.

These acids ultimately dissolve the hydroxyapatite crystals which form the tooth enamel and invade the tooth dentin. At that time the tooth requires restoration, and such restoration is typically accomplished by drilling the decay from the tooth and thereafter filling the tooth. Since the tooth decay diffuses under the enamel and into the dentin, a portion of the enamel around the point of penetration usually must also be removed during the drilling process.

There have been a number of previously known experiments in which teeth have been subjected to laser irradiation to determine the alteration, if any, of the physical and/or chemical properties of the dental enamel. These studies have shown that the hydroxyapatite crystals that form the enamel fuse somewhat at the surface when lased and renders the enamel more impervious to acids of the type which cause tooth decay. These previous studies, however, have also concluded that the use of a laser cannot be used to remove tooth decay since the power level necessary for the laser to burn through the enamel also significantly heats the tooth and can kill the tooth nerve. For this reason, lasers have not been previously used to remove tooth decay.

SUMMARY OF THE PRESENT INVENTION

The present invention provides a method for removing decay from teeth and particularly human teeth.

In brief, the method of the present invention comprises the steps of aiming a pulsed laser at the decay and thereafter repeatedly activating the laser until the decay is eradicated from the tooth. Preferably, the laser is a yttrium-aluminum-garnet laser having a pulse width of about 50-2000 microns, a pulse duration of a picosecond to several milliseconds and an energy of 0.1-100 millijoules. The laser can be either a single shot laser which requires actuation by the user for each laser activation, or a repetitive laser in which the laser is activated at a predetermined frequency rate per user actuation. This frequency rate, moreover, is oftentimes user adjustable.

The precise physical process by which the laser obliterates the tooth decay without heating the tooth and endangering the nerve is not entirely understood. However, it is believed that the high energy laser beam coupled with its short pulse duration essentially vaporizes tooth decay.

The present invention further provides a method for removing disease from soft tissue, such as gum tissue. Furthermore, such removal is painless.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which.

DETAILED DESCRIPTION OF A PREFERRED EMBODIMENT OF THE PRESENT INVENTION

Figure 1:
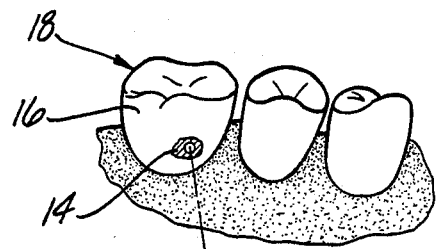
FIG. 1 is a perspective view illustrating the apparatus employed to carry out the method of the present invention.

With reference first to FIG. 1, an apparatus for carrying out the method of the present invention is thereshown and comprises a laser 10 which, upon activation, generates a laser beam 12. The laser 10 is a pulse laser and preferably is a yttrium-aluminum-garnet laser which produces an energy output of 0.1-100 millijoules for a duration of between several picoseconds and several milliseconds and with a beam diameter of 50-2000 microns.

Figure 2:
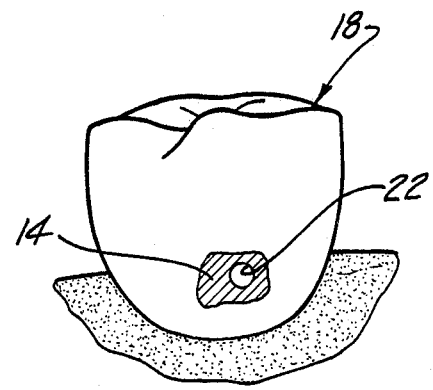
FIG. 2 and 3 are diagrammatic views illustrating steps of the preferred embodiment of the present invention.
Figure 4:
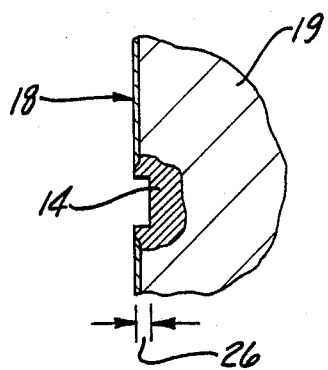
FIG. 4 is a cross-sectional view taken substantially along line 4—4 in FIG. 3.

With reference now to FIGS. 1, 2 and 4, the laser 10 is employed to remove tooth decay 14 in a tooth 18 which, as shown in FIG. 4, has invaded the tooth dentin 19. The laser output beam 12 is aimed at the decay 14 through any conventional delivery system 20, such as an optical fiber bundle.

Any conventional aiming system, such as a helium neon laser aiming system, can be used to aim or focus the laser output beam 12.

Figure 3:
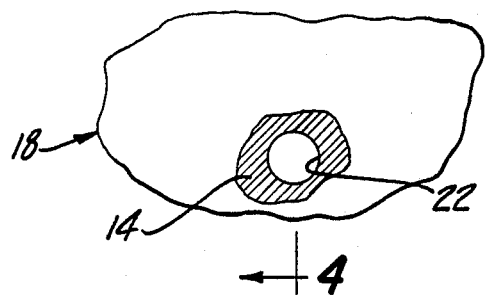

With reference now to FIGS. 2-4, upon activation of the laser 10, the laser eradicates by varporization the tooth decay 14 in the area 22 of the laser beam impingement and to a depth 26 (FIG. 4) into the decay 14 in the dentin 19. Thereafter, the laser 10 is reaimed through the delivery system 20 to the remaining portions of the tooth decay 14 and reactivated until the entire decay 14 is eradicated or obliterated from the tooth.

The energy level of the laser 10 is preferably adjustable to produce power levels between 0.1 and 100 millijoules which correspondingly varies the depth 26 of decay 14 obliterated by the laser 10. For shorter tooth decay, relatively lower laser powers are used and vice versa.

The precise phenomenon which occurs when the tooth is lased and the decay obliterated is not understood due to the extremely short time period involved during the lasing operation. It has been found, however, that the decay is obliterated without significantly heating the tooth and thus without damage to the nerve.

As best shown in FIG. 2, the present invention also provides a method for removing disease 30 from soft tissue 32, such as gum tissue. In this method, the laser having the same energy level, pulse duration and pulse diameter previously described is aimed at the diseased portion of the soft tissue and activated. Once activated, the diseased portion 30 of the soft tissue 32 is obliterated thus removing the disease and sterilizing the soft tissue. Repeated activations of the laser may be required in order to completely eradicate the diseased portion 30 of the soft tissue 32 and the removal of the diseased portion 30 is painlessly accomplished.

Having described my invention, however, many modifications thereto will become apparent to those skilled in the art to which it pertains without deviation from the spirit of the invention as defined by the scope of the appended claims.

I claim:

1. A method for removing tooth decay that has invaded the dentin from a tooth comprising the steps of:
    aiming a pulsed laser so that the output from the laser impinges upon the tooth decay,
    repeatedly activating the laser until the tooth decay is removed from the tooth,
    wherein said laser has an energy output in the range of 0.1 to 100 millijoules per pulse and a pulse duration of between several picoseconds and several milliseconds.

2. The invention as defined in claim 1 wherein said laser is a yttrium-aluminum-garnet laser.

3. The invention as defined in claim 2 wherein said focusing step further comprises the step of focusing said laser to a beam diameter of between 50 and 2000 microns.

4. The invention as defined in claim 1 wherein said aiming step further comprises the step of passing the laser beam through an optical delivery system.

5. A method for removing disease from soft gum tissue comprising the steps of:
    aiming a pulsed laser so that the output from the laser impinges upon the diseased soft gum tissue,
    repeatedly activating the laser until the diseased soft gum tissue is eradicated,
    wherein said laser has an energy output in the range of 0.1 to 100 millijoules per pulse and a pulse duration of between several picoseconds and several milliseconds.

6. The invention as defined in claim 5 wherein said laser is a yttrium-aluminum-garnet laser.

7. The invention as defined in claim 6 wherein said focusing step further comprises the step of focusing said laser to a beam diameter of between 50 and 2000 microns.

8. The invention as defined in claim 5 wherein said aiming step further comprises the step of passing the laser beam through and optical delivery system.

* * * * *